(12) United States Patent
Lindner

(10) Patent No.: US 9,089,132 B2
(45) Date of Patent: Jul. 28, 2015

(54) AGROCHEMICAL ADJUVANTS AND FORMULATIONS

(75) Inventor: Gregory James Lindner, Wilmington, DE (US)

(73) Assignee: Croda, Inc., Edison, NJ (US)

( * ) Notice: Subject to any disclaimer, the term of this patent is extended or adjusted under 35 U.S.C. 154(b) by 5 days.

(21) Appl. No.: 13/817,323

(22) PCT Filed: Aug. 16, 2011

(86) PCT No.: PCT/US2011/047882
§ 371 (c)(1),
(2), (4) Date: May 29, 2013

(87) PCT Pub. No.: WO2012/024276
PCT Pub. Date: Feb. 23, 2012

(65) Prior Publication Data
US 2013/0244877 A1  Sep. 19, 2013

Related U.S. Application Data

(60) Provisional application No. 61/344,547, filed on Aug. 17, 2010.

(51) Int. Cl.
| | | |
|---|---|---|
| A01N 43/08 | (2006.01) | |
| A01N 25/30 | (2006.01) | |
| A01N 35/10 | (2006.01) | |
| A01N 57/20 | (2006.01) | |
| C07D 307/20 | (2006.01) | |
| C07D 309/10 | (2006.01) | |
| A01N 43/88 | (2006.01) | |

(52) U.S. Cl.
CPC ............. *A01N 43/08* (2013.01); *A01N 25/30* (2013.01); *A01N 35/10* (2013.01); *A01N 57/20* (2013.01); *C07D 307/20* (2013.01); *C07D 309/10* (2013.01)

(58) Field of Classification Search
USPC .......... 504/299, 292, 294; 514/473, 451, 640; 549/478, 417, 423, 429, 476; 554/1, 554/213; 560/129, 61, 103; 564/253
See application file for complete search history.

(56) References Cited

U.S. PATENT DOCUMENTS

| | | | | |
|---|---|---|---|---|
| 4,297,290 A | * | 10/1981 | Stockburger | 549/478 |
| 5,863,909 A | * | 1/1999 | Kurita et al. | 514/129 |
| 6,375,977 B1 | * | 4/2002 | Auguste et al. | 424/447 |
| 6,599,392 B1 | * | 7/2003 | Tadokoro et al. | 162/158 |

FOREIGN PATENT DOCUMENTS

| | | | | |
|---|---|---|---|---|
| EP | 0729700 | 9/1996 | | |
| EP | 2181594 | 5/2010 | | |
| WO | WO 96/16539 | 6/1996 | | |
| WO | WO96/16539 A1 | * 6/1996 | ............. | A01N 25/30 |
| WO | WO 99/29171 | 6/1999 | | |
| WO | WO 2006/050141 | 5/2006 | | |
| WO | WO2006/050141 A1 | * 5/2006 | ............. | A01N 25/30 |
| WO | WO 2010/003889 | 1/2010 | | |
| WO | WO2010/003889 A1 | * 1/2010 | ............. | A01N 39/04 |

OTHER PUBLICATIONS

Search Report from corresponding Taiwan Patent Application No. 100127786, dated Jan. 6, 2015.
International Search Report dated Dec. 15, 2011 for corresponding PCT/US2011/047882.
Abstract No. XP002665156 from Chemical Abstracts Service Database Registry, Database Accession No. 1052282-29-7 (Sep. 24, 2008).

* cited by examiner

*Primary Examiner* — Jane C Oswecki
(74) *Attorney, Agent, or Firm* — Jones Day

(57) ABSTRACT

Ethoxylated fatty acid mono-ester(s) of sorbitan with a fatty acid chain length from 8 to 14 and an overall degree of ethoxylation from 7 to 16 are new (though related to the polysorbates). These compounds are useful as adjuvants in agrochemical formulations, particularly combination formulations of herbicides having differing weed control effects, notably of non-selective herbicide and selective herbicide; particularly selective herbicide, particularly selective broadleaf herbicide, and graminicide; and selective graminicide and non-selective herbicide, especially a combination of a glyphosate type non-selective water soluble herbicide with a clethodim type selective (graminicide) herbicide, particularly to reduce or eliminate antagonism between differing types of herbicide. Formulations including such herbicide combinations and the adjuvant compounds are particularly useful in controlling weed including volunteer glyphosate resistant maize in subsequently sown glyphosate resistant soya.

15 Claims, No Drawings

AGROCHEMICAL ADJUVANTS AND FORMULATIONS

CROSS REFERENCE TO RELATED APPLICATIONS

This application is the National Phase of International Application No. PCT/US2011/047882, filed Aug. 16, 2011 in English, and which further claims the benefit of priority from U.S. Provisional Application No. 61/344,547, filed Aug. 17, 2010. The foregoing related applications, in their entirety, are incorporated herein by reference.

The present invention relates to adjuvants for agrochemical formulations, to formulations including such adjuvants, and to the treatment of crops with such formulations.

In co-formulated agrochemicals some combinations of agrochemical actives do not work as well as expected when compared to the properties of the individual agrochemically active components. The effect appears to be an antagonism between the agrochemically active components. This is not fully understood, but seems not to be merely a physical formulation incompatibility (though physical incompatibility may also be present and contribute to lower than expected performance), but the result of a biological/biochemical antagonism having complex mechanisms. Such antagonisms can practically interfere with what would otherwise be advantageous co-formulations of agrochemical actives. It may be possible to overcome this difficulty by spraying with each active separately, with a suitable time interval, or by using additional or special crop oil adjuvants, but all of this adds time and cost.

One area where antagonism is commercially important is between selective broadleaf herbicides and graminicides (postemergent grass herbicides). The data suggests physical interaction between differing forms of the active ingredients and complex interactions between salt and acid forms of either or both herbicides, with a resulting change in the absorption or uptake of the graminicide into the target. In some cases doubling of graminicide rates were required to effect grass control.

A particular form of this antagonism arises in growing herbicide, particularly glyphosate, resistant crops, where glyphosate is used as a general herbicide with benefit to the desired crop precisely because of its glyphosate resistance. Rotating such crops means that glyphosate is ineffective in suppressing a resistant crop growing as volunteer plants in the succeeding (different but still glyphosate resistant) crop, potentially undermining the main advantage in using herbicide tolerant crop species.

This problem can be met by using combinations of herbicides, typically glyphosate to suppress general weeds and another herbicide, to suppress the volunteer (glyphosate resistant) prior crop. Thus growing glyphosate resistant soya in succession to glyphosate resistant maize, it is possible to use a combination of glyphosate and a graminicide such as clethodim, a herbicide effective against grasses including maize but not herbicidally active against broadleaved plants such as soya.

Whilst this combination can give the right activity profile to suppress volunteer (glyphosate resistant) maize and general weeds in (glyphosate resistant) soya, unfortunately glyphosate and clethodim can be antagonistic to each other particularly when co-applied in a single spray formulation and therefore reducing overall effectiveness. A similar antagonism has been noted between glufosinate and clethodim type herbicides. Further similar antagonism has been noted with some broadleaf herbicides such as bentazon, bromoxynil and 2,4-D amine with graminicides including clethodim, quizalofop and sethoxydim.

Conventional non-ionic surfactant adjuvants, at application rates common for such adjuvants, appear to be relatively ineffective in boosting combined herbicide performance to overcome such antagonism between the actives.

The present invention therefore seeks to provide adjuvants which can reduce antagonism between active combinations, particularly when used with herbicide actives, and thereby can overcome the disadvantages of the prior co-formulated agrochemicals as described herein.

The present invention further seeks to provide an agrochemical concentrate and agrochemical spray tank mixes comprising said adjuvants, and treatment of crops using said concentrate and tank mixes, particularly when using combinations of agrochemical actives which would otherwise exhibit antagonism.

According to a first aspect of the present invention there is provided a compound or mixture of compounds which is/are ethoxylated fatty acid mono-esters of sorbitan in which the carbon chain length of the fatty acid is from 8 to 14, and the overall degree of ethoxylation is on average from 7 to 16.

Surprisingly, it has been found that certain novel surfactants can provide adjuvancy which largely overcomes herbicidal performance antagonism, and may do so in a cost effective manner. The novel surfactants are variants of the known ethoxylated sorbitan mono-ester surfactants known as "polysorbates", for example those available under the trademark "Tween" from Croda.

Historically, polysorbate surfactants have contained either relatively low degree of ethoxylation, typically corresponding to an average of about 4 or 5 oxyethylene residues per molecule, or have an average of about 20 oxyethylene residues per molecule. The 5-ethoxylate sorbitan esters are somewhat less hydrophobic than the low HLB (hydrophilic-lipophilic balance) sorbitan ester surfactants, such as those available under the trademark "Span" (from Croda), from which they are usually derived by ethoxylation.

In contrast, the 20-ethoxylate sorbitan esters are hydrophilic surfactants typically with HLB values of about 15 or higher. These more highly ethoxylated polysorbates, such as Tween 20 (sorbitan monolaurate 20-ethoxylate), have been widely used in agrochemical formulations as adjuvants and as emulsifiers.

The carbon chain length of the fatty acid of the ethoxylated fatty acid mono-esters of sorbitan may preferably be from 10 to 14. More preferably, the carbon chain length is about 12.

The overall degree of ethoxylation may on average preferably be from 8 to 12. More preferably, the overall degree of ethoxylation may be on average about 10.

The ethoxylated fatty acid mono-esters of sorbitan are preferably compounds of formula (I):

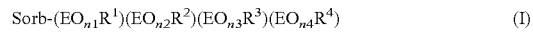

$$\text{Sorb-}(EO_{n1}R^1)(EO_{n2}R^2)(EO_{n3}R^3)(EO_{n4}R^4) \quad (I)$$

wherein
 i) Sorb represents a residue obtained by removing four hydroxyl H atoms from sorbitan;
 i) EO represents an ethyleneoxy residue;
 ii) n1, n2, n3, and n4 each independently represent average values from 0 to 10, preferably 0.5 to 5;
 iii) the total n1+n2+n3+n4 has an average value from 7 to 16, particularly 8 to 12; and
 iv) $R^1$, $R^2$, $R^3$, and $R^4$ each independently represents H or an acyl group —C(O)—$R^5$, where $R^5$ is a $C_7$ to $C_{13}$ hydrocarbyl, more usually $C_9$ to $C_{13}$ hydrocarbyl, particularly about $C_{11}$ hydrocarbyl, particularly alkyl or alkenyl, especially linear alkyl or alkenyl, group.

It is to be understood that the sorbitan residue is obtainable by removal of the four hydroxyl H atoms, and the ethoxylated fatty acid mono-ester formed by each of the removed H atoms being substituted with the groups $(EO_{n1}R^1)$, $(EO_{n2}R^2)$, $(EO_{n3}R^3)$, and $(EO_{n4}R^4)$.

Preferably, an average of 2.8 to 3.2 of the $R^1$, $R^2$, $R^3$, and $R^4$ groups are H and 0.8 to 1.2 of the $R^1$, $R^2$, $R^3$, and $R^4$ groups are acyl groups —C(O)—$R^5$.

In the compounds of the invention, the sorbitan residue at the core of the molecule, corresponding to the residue 'Sorb' in formula (I), will typically be a mixture mainly of residues of 1,4-anhydrosorbitol, 1,5-anhydrosorbitol, and 3,6-anhydrosorbitol.

The mixture may also typically include some 1,4,3,6-dianhydrosorbitol (iso-sorbide), though the proportion of iso-sorbide if present is usually relatively low because the ethoxylated products from iso-sorbide esters may be less useful surfactants.

1,4-anhydrosorbitol and 3,6-anhydrosorbitol residues (without the hydroxyl hydrogen atoms) can be considered as being of the formula (IIa):

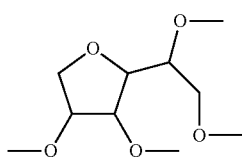

(IIa)

The difference between the 1,4- and 3,6-isomers being in the orientations of the —O— groups at the chiral carbon atoms.

1,5-anhydrosorbitol residues (without the hydroxyl hydrogen atoms) can be considered as being of the formula (IIb):

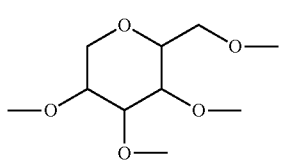

(IIb)

The corresponding ethoxylated "core" residues (i.e. without showing terminating groups $R^1$, $R^2$, $R^3$, and $R^4$) may be envisaged for the above mentioned sorbitan isomers as of the formulae (IIa') and (IIb') as follows:

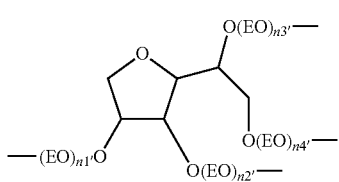

(IIa')

-continued

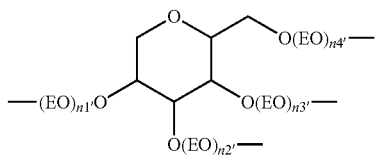

(IIb')

where n1', n2', n3', and n4' are as defined for n1, n2, n3, and n4 in formula (I) above (with no necessary correspondence between indices sharing numbers).

The esters of and used in the invention are desirably mono-esters. It is found that the solution behaviour and wetting properties of mono-esters are superior particularly in agro-chemical adjuvant applications. In this general type of ethoxylated sorbitan ester compound, nominal mono-esters are so called because the molar ratio of sorbitol to fatty acid used to make the sorbitan ester precursor of the ethoxylated esters is approximately 1:1, although it is usual to employ a modest excess e.g. from 5 to 10% molar, of the fatty acid.

The cyclisation reaction (as described herein) will result in some products including sorbitol and iso-sorbide residues, as well those with sorbitan residues. Additionally the 'mono-esters' (and the corresponding ethoxylated derivatives) will include small proportions of compounds including unesterified polyol (sorbitol/sorbitan/iso-sorbide) residues, substantial proportions of mono- and di-fatty acyl esters, mainly of sorbitan, but including modest based on iso-sorbide and small proportions based on sorbitol, with some level of tri- and higher esters mainly based on sorbitan. This contrasts with the nominal "triesters" of sorbitan which contain major proportions of tri- and higher esters. Of course the range of individual compounds after ethoxylation will be even greater.

On initial esterification, it may be understood that the majority of the acyl residues react with primary hydroxyls in the sorbitol or sorbitan (corresponding to the 1- or 6-positions in sorbitol), but that during subsequent processing trans-esterification largely randomises the position of the acyl group(s). The ethoxylation will involve further trans-esterification so further randomising the acyl positions.

In the context of the compounds of formula (I) that the compounds are mono-esters generally means that the relative (molar) amounts of fatty acid and (normally) sorbitol used to make the intermediate sorbitan ester (see further below on synthesis) will approximately correspond to making a mono-ester.

Thus desirably, for each mole of sorbitan in the compounds of the invention as represented by formula (I), there will generally be on average from 0.8 to 1.2 acyl residues substituent on the sorbitan; i.e. referring to formula (I) from 0.8 to 1.2 of the groups $R^1$, $R^2$, $R^3$, and $R^4$ are acyl groups of the formula —C(O)—$R^5$, and correspondingly 2.8 to 3.2 of the groups are hydrogen atoms. However, as noted above, esters with more than one acyl groups will also usually be present in the products as synthesised.

The average degree of ethoxylation of the compounds of the invention, corresponding to the total n1+n2+n3+n4 in formula (I) [or n1'+n2'+n3'+n4' in formulae (IIa') and (IIb')], is from 7 to 16, particularly from 8 to 12, and especially about 10. This preference reflects the performance that has been observed in testing the compounds of the invention.

Generally, as made by ethoxylation of the corresponding sorbitan fatty acid ester, the individual oligoethoxylate chain lengths corresponding to the individual indices n1, n2, n3, and n4 in formula (I) [or n1', n2', n3', and n4' in formulae (IIa')

and (IIb')] will each be within the range from 0 to 10, more usually from 1 to 6, particularly from 1 to 4.

The individual chain lengths may depend on whether the underlying OH group is primary or secondary, and the effect of steric hindrance (which will vary depending on the position of the underlying OH group and the extent of ethoxylation, particularly on adjacent OH groups). Further, as the indices represent average values for the polyethyleneoxy chain lengths, they may individually and in total be non-integral.

It has been found that away from the range 'centres', particularly for the overall degree of ethoxylation, the performance of the compounds of the invention falls away from the maximum. This may be observed when use particularly as agrochemical adjuvants, especially in combination formulations including non-selective herbicide (such as glyphosate) and selective graminicide (such as clethodim).

The fatty acid residue in the compounds of the invention, corresponding to the acyl group —C(O)R$^5$ in formula (I), is a $C_8$ to $C_{14}$, particularly $C_{10}$ to $C_{14}$, more particularly about a $C_{12}$, fatty acid residue. As applied to practically available technical grade fatty acids, these ranges represent the average carbon chain length (which for any particular material may therefore be non-integral). Generally the chain length of the individual fatty acids in any such mixture will desirably be within 2 carbon atoms of the average. A particularly useful source of such acyl residues is technical grade lauric acid, typically derived from coconut oil which is a mixture of fatty acids having chain lengths predominantly from $C_8$ to $C_{14}$.

The compounds of and used in the invention can be made by methods generally known in the art for corresponding known compounds—the polysorbates. In particular, they may be made from sorbitan esters, which are known generally as a class, by reaction with ethylene oxide usually under basic catalysis. Base catalysis may be provided by sodium or potassium hydroxide or methoxide. The ethoxylation reaction may be carried out at a temperature typically from 150 to 180° C. and at a pressure of from 400 to 650 kPa (gauge).

The sorbitan esters, used as starting materials for the ethoxylation reaction making the compounds of the invention, are generally known and may themselves be made by reacting sorbitol with a suitable fatty acid to form the sorbitan ester by anhydridisation cyclisation of the sorbitol to sorbitan and esterification. The suitable fatty acid comprises from 8 to 14 carbon chain length, preferably from 10 to 14, and more preferably about 12.

This reaction can be carried out by catalysed direct reaction of sorbitol and the fatty acid at a temperature typically from 225 to 250° C. and at ambient or near ambient pressure under base, acid, or buffered acid catalysis. Further information on the synthesis of this general type of surfactant can be found in standard text books on non-ionic surfactants such as Surfactant Science Volume 1: Nonionic Surfactants (pub. 1967 by Marcel Dekker) particularly the chapter by F R Benson titled "Polyol Surfactants".

The ethoxylated fatty acid mono-esters of sorbitan may be particularly included in agrochemical formulations comprising at least one agrochemical active.

Thus, according to a second aspect of the present invention there is provided an agrochemical formulation, wherein the formulation comprises at least one ethoxylated fatty acid mono-esters of sorbitan in which the carbon chain length of the fatty acid is from 8 to 14, and the overall degree of ethoxylation is on average from 7 to 16, and wherein the agrochemical formulation comprises at least one agrochemical active.

According to a third aspect of there is provided the use of fatty acid mono-esters of sorbitan of the first aspect as adjuvants in an agrochemical formulation, wherein the agrochemical formulation comprises at least one agrochemical active.

It is to be understood that references to adjuvant(s) in relation to agriculture refer to any substance added to the concentrate or the spray tank that will improve the performance of the agrochemical active components (pesticides, herbicides, feeding stimulants etc). Adjuvants for use with agricultural actives have been categorised as extenders, wetting agents, sticking agents, and fogging agents.

The agrochemical formulation may be an agrochemical concentrate formulation. Alternatively, the agrochemical formulation may be an agrochemical spray formulation which is formed by dilution of said concentrate formulation, or formed directly by addition of all the necessary components with water to form the dilute mixture.

The agrochemical spray formulation may be formed by dilution of the agrochemical concentrate formulation with the necessary amount of water to achieve the desired dilution.

The agrochemical spray formulation may be made up just prior to spraying by diluting the concentrate in the spray water. The compounds of the invention may be included as adjuvants by inclusion in a pre-formed separate agrochemical active concentrate, or as components in the agrochemical concentrate formulation, or added separately to the tank mix.

The agrochemical formulation may also include additional ingredients such as surfactants, adjuvants other than those of the first aspect, antifreeze materials, buffering materials, and so forth.

The agrochemical formulation comprises at least one agrochemical active. Said active may be selected from herbicidal active compounds, fungicidal active compounds, insecticidal (acaricidal) active compounds, or plant growth controlling compounds.

Preferably the agrochemical formulation comprises at least two agrochemical actives. The actives may be selected from the same group of compounds, or alternatively may be selected from two or more separate groups of compounds.

The combination of two or more agrochemical actives may be termed a co-formulation. Particularly preferred co-formulations may comprise a combination of agrochemical actives, each of which is a herbicidal active compound, and each having differing weed control effects.

The co-formulation would additionally include compounds of the first aspect of the invention as an adjuvant.

Preferably, the compounds of the first aspect are envisaged as being used in formulations comprising agrochemical actives which are herbicides having differing weed control effects. In particular, combinations of a non-selective herbicide and another agrochemical active, preferably selected from another type of herbicide, more preferably a selective herbicide.

Suitable combinations of actives may be selected from a selective herbicide and a graminicide, particularly a non-selective herbicide; a selective broadleaf herbicide and a graminicide, which may be either an ACCase inhibitor or a non-selective herbicide; and a selective graminicide, particularly an ACCase inhibitor used in combination with a non-selective herbicide.

The invention finds particular use in combination systems of non selective herbicides, such as glyphosate, and selective graminicides such as clethodim [(±)-2-[(E)-I-[(E)-3-chloro-allyloxyamino]propyl]-5-[2-(ethylthio)propyl]-3-hydroxy-cyclohex-2-enone)]. In such combinations it is found that compounds of the first aspect of the invention are usable to counteract the antagonism between glyphosate and cyclohex-anedione (lipid inhibitor) type herbicides.

Further, suitable co-formulations, for which the compounds of the first aspect may be used with, may include combinations of actives selected from:
i) a non-selective herbicide used in combination with another type of agrochemical active, particularly another type of herbicide, more particularly a selective herbicide;
ii) a selective herbicide used in combination with a graminicide particularly a non-selective graminicide;
iii) a selective broadleaf herbicide used in combination with a graminicide, which may be a selective graminicide such as a cyclohexanedione e.g. clethodim, or a non-selective herbicide; and
iv) a graminicide such as a cyclohexanedione e.g. clethodim, used in combination with a non-selective herbicide.

The non-selective herbicides which can be used in these aspects of the invention include water soluble herbicides such as glyphosate, particularly as alkali metal, amine or trimesium salts, glufosinate, particularly as alkali metal, amine or ammonium salts and bipyridyl herbicides, particularly paraquat and diquat.

Other suitable non-selective herbicides include acetyl-CoA carboxylase (ACCase) inhibitors, such as aryloxyphenoxy-(particularly phenoxyphenoxy-) and heteroaryloxyphenoxy-propionic acids and their esters and salts (FOPs) and cyclohexanedione oximes; hydroxyphenylpyruvate dioxygenase (HPPD) inhibitors, such as isoxazoles, triketones, pyrazoles, benzobicyclon and ketospiradox; acetolactate synthase (ALS) inhibitors, such as sulfonylureas, imidazolinones, triazolopyrimidines, pyrimidinyl oxybenzoates, and sulfonylamino carbonyl triazolinones; polyphenol oxidase (PPO) inhibitors, such as triazolinone (for example carfentrazone-ethyl), phenylpyrazole (for example pyraflufen-ethyl), N-phenylphthalimides (for example flumiclorac), and thiadiazoles (for example fluthiacet-methyl); synthetic auxins such as 2,4-dichlorophenoxyacetic acid (2,4-D) and 2,4,5-trichlorophenoxyacetic acid (2,4,5-T); and growth regulators.

The invention particularly includes a combination formulation of a glyphosate type non-selective water soluble herbicide with a selective herbicide, commonly a graminicide, preferably an acetyl CoA carboxylase inhibitor such as an aryloxyphenoxy-propionate (FOP) or cyclohexanedione (DIM) type herbicide, particularly quizalofop ((R)-2-[4-(6-chloroquinoxalin-2-yloxy)phenoxy]-propionic acid) or more particularly clethodim ((±)-2-[(E)-I-[(E)-3-chloroallyloxyamino]propyl]-5-[2-(ethylthio)propyl]-3-hydroxy-cyclohex-2-enone)), and including a compound of the invention as an adjuvant. The use of such combinations can enhance the control of glyphosate tolerant grass species, more particularly glyphosate tolerant maize e.g. as volunteer plants, in a subsequently grown glyphosate tolerant broadleaf crop, particularly glyphosate tolerant soya.

Glyphosate type herbicides are widely used agrochemicals and usually take the form of salts, particularly alkali metal, especially sodium or potassium, or amine, particularly isopropylamine, ammonium or trimesium (trimethylsuiphonium), salts. These salts are highly water soluble and glyphosate is usually supplied for use as a concentrated solution in water typically at from 10 to 60, particularly 25 to 50, and especially 30 to 50 g (active). $l^{-1}$ (solution) (glyphosate free acid equivalent).

Cyclohexanedione (lipid inhibitor) selective herbicides are active against grasses and are oil soluble compounds with Clethodim typically provided as a solution in a suitable organic solvent commonly in hydrocarbon solvent such as Aromatic or Solvesso 150 fluids from Shell or, other solvents/cosolvents such as dimethyl fatty alkylamides, at concentrations of from 50 to 500, particularly 60 to 480, and especially 120 to 360, g (active). $l^{-1}$ (solution). These oil based solutions will commonly include oil soluble emulsifier surfactant at a concentration sufficient to emulsify the oil solution on dilution in water i.e. to provide an emulsifyable concentrate. The emulsifier will typically be a non-ionic and anionic blend type emulsifier and will be present in the concentrate typically at from 1 to 25, particularly 5 to 20, and especially 8 to 15, g (emulsifier). $l^{-1}$ (concentrate).

The main use that is envisaged for the compounds of the first aspect is as adjuvants in agrochemical formulations, particularly in formulations comprising more than one active, to counteract the antagonism between the different types of agrochemical active.

Thus, according to the fourth aspect of the present invention there is provided a method of treatment of crops and/or the soil around crops with the agrochemical formulation of the second aspect.

The invention accordingly includes the use of such agrochemical formulations to treat crops, including to fertilise crops and to kill weeds in crops or pests on crops.

The agrochemical formulation used in the method of treatment may be selected from an agrochemical spray formulation. Said spray formulation may be a diluted concentrate formulation or a tank mix spray formulations. The invention therefore further provides a method of treating crops or soil adjacent to crop plants or soil in which crops are to be grown with a spray formulation which is or includes a diluted agrochemical concentrate formulation.

The agrochemical spray formulation may be a homogeneous stable liquid which is capable of forming a stable dilution with water.

The agrochemical formulation used in the method of treatment will generally be used to treat crops or land where crops are to be grown, and may perform the function of fertilising crops and/or killing weeds in or pests on crops.

All of the features described herein may be combined with any of the above aspects, in any combination.

In order that the present invention may be more readily understood, reference will now be made, by way of example, to the following description. The following Examples illustrate the invention. All parts and percentages are by weight unless otherwise stated.

Materials—sorbitan monolaurate made using technical grade lauric acid, Span 20 ex Croda Test Methods Hydroxyl Value—Hydroxyl groups in a test sample are acetylated with a known amount of acetic anhydride in pyridine; remaining acetic anhydride is hydrolysed with water and back titrated with standard ethanolic KOH solution with phenophthalein indicator. Hydroxyl Value is the amount of base (milligrams KOH) required to neutralise the acid used to acetylate the OH groups in 1 g of sample. Free acid in the sample increases the consumption of KOH in titration to give a falsely low Hydroxyl Value, so the Acid Value (see below) is added to the result. The results are quoted as "OH Value" in mg(KOH)·g (sample)$^{-1}$.

Acid Value—a test sample dissolved in a suitable solvent (usually ethanol) is titrated against standard (usually ethanolic) KOH solution with phenophthalein indicator. Acid Value is amount of base (as milligrams KOH) required to neutralize the fatty acids in 1 g of sample. The results are quoted as "Acid Value" in mg (KOH)·g (sample)$^{-1}$. [Note: in assessing a sample for the weight of fatty acid present, the molecular weight of the fatty acid needs to be allowed for and for mixtures this will usually be an intermediate value depending on the range of homologues present.]

Saponification Value—a test sample dissolved in a suitable solvent (usually ethanol) is refluxed with a known quantity of standard ethanolic KOH to hydrolyse esters present and neutralise the fatty acids liberated (and any free fatty acids present in the test sample). The excess KOH remaining after hydrolysis is back titrated with standard aqueous HCl. Saponification Value is the amount of base (as milligrams KOH) required to neutralise the fatty acids resulting from saponifying a 1 g sample (including any contribution from free fatty acid in the sample). The results are quoted as "SAP Value" in mg (KOH)·g (sample)$^{-1}$.

SYNTHESIS EXAMPLES

Synthesis Example SE1

Sorbitan monolaurate 8-ethoxylate

A clean, dry 1 liter pressure reactor equipped with an agitation nitrogen sweep, thermometer and vacuum supply was purged with dry nitrogen for 10 to 15 minutes; sorbitan monolaurate (202.8 g; 0.167 mol) and 50% wt aqueous NaOH solution as catalyst (0.4 g) were charged at ambient temperature. The reactor was heated slowly to 160° C. with the agitation sweep on and during the heating vacuum was applied to aid water removal. Once the residual water fell below 0.2% at a temperature from 160 to 165° C., the sweep agitation was stopped.

Ethylene oxide (total 58 g; 1.32 mol) was fed into the reactor at from 150 to 165° C. at a rate controlled to keep the reactor pressure below 60 psig (ca. 414 kPa gauge). On completion of ethylene oxide addition, the reactor pressure was allowed to decrease (from completion of the ethoxylation reaction) while holding at the reaction temperature at from 160 to 165° C., until the pressure reached a steady low value after which the mixture was held for a further 2 hours. The reactor was then cooled to 120° C. and a steam (or nitrogen) sparge was applied for 10 to 20 minutes to remove residual ethylene oxide. The reaction mixture was cooled to 60 to 65° C. and the product discharged.

Synthesis Examples SE2 and SE3

Further ethoxylated sorbitan esters were made with different degrees of ethoxylation using the method of Synthesis Example SE1, but suitably varying the amount of ethylene oxide supplied to the reaction.

The properties of the compounds synthesised are summarised in Table SE1 below.

TABLE SE1

| Ex No | Fatty Acid | EO (mol)* | OH Value [mg(KOH)·g$^{-1}$] | Acid Value [mg(KOH)·g$^{-1}$] | SAP Value [mg(KOH)·g$^{-1}$] |
|---|---|---|---|---|---|
| SE1 | lauric | 8 | 175.6 | 0.33 | 78.6 |
| SE2 | lauric | 12 | 138.2 | 0.51 | 60.9 |
| SE3 | lauric | 16 | 119.6 | 0.64 | 53.7 |

*average moles EO per mole of sorbitan ester

APPLICATION EXAMPLES

Materials

Gly glyphosate herbicide as Touchdown Hi-Tech ex Monsanto
Cle clethodim herbicide as Select ex Arysta LifeScience Corp
AMS ammonium sulphate as 100% material
Adj1 sorbitan laurate 4-EO, polysorbate 21, Tween 21 ex Croda
Adj2 sorbitan laurate 20-EO, polysorbate 20, Tween 20 ex Croda Test Methods The ability of the compounds of the invention to act as adjuvants improving the combined herbicide performance of glyphosate and clethodim was assessed. The trials tested the combined herbicide on glyphosate resistant soya and glyphosate resistant maize, using various adjuvants including controls and compounds of the invention. The aim was to enable assessment of the ability of the combined herbicide to control the growth of volunteer maize in glyphosate resistant soya grown as a crop in rotation following a previous crop of the glyphosate resistant maize.

Application Example AE1

Formulation details—Herbicide formulations were made up as spray tank mixes using the following components:

| Material | Concentration (wt. %) | Notes |
|---|---|---|
| Gly | 0.3 | % glyphosate free acid equivalent |
| Cle | 0.025 | % of active ingredient |
| Adjuvant | variable | |
| AMS | 0.42 | |

Formulations containing adjuvants of the invention were made up with 0.0625, 0.125 and 0.25% by wt. of adjuvant (AE1.1, AE1.2 and AE1.3—the adjuvants being identified by their SE nos). Control samples included no treatment (AE1C.1); and formulations including both glyphosate and clethodim as herbicides but using conventional "Tween" surfactants (Adj1 and Adj2) as adjuvants (AE1C.2 and AE1C.3).

Summary treatment conditions—sprayed at 15 US gallons per acre=ca 23 liter per hectare on glyphosate resistant maize. Parallel spray tests were run using glyphosate resistant soya as the target crop and no toxicity was noted at any level of application. This was the expected result as the soya is glyphosate resistant and being a broadleaf plant is not susceptible to clethodim.

The results of field testing are set out in Table AE1 below.

TABLE AE1

| | Adjuvant | | | Control (% kill) | |
|---|---|---|---|---|---|
| Ex No | Type | EO No | rate (%) | 14-day | 28-day |
| AE1C.1 | none | — | 0.0625 | 0 | 0 |
| | | | 0.125 | 0 | 0 |
| | | | 0.25 | 0 | 0 |
| AE1C.2 | Adj1 | 4 | 0.0625 | 50 | 48 |
| | | | 0.125 | 59 | 76 |
| | | | 0.25 | 56 | 71 |
| AE1.1 | SE1 | 8 | 0.0625 | 54 | 52 |
| | | | 0.125 | 64 | 83 |
| | | | 0.25 | 71 | 80 |
| AE1.2 | SE2 | 12 | 0.0625 | 45 | 38 |
| | | | 0.125 | 61 | 73 |
| | | | 0.25 | 63 | 82 |

TABLE AE1-continued

| Ex No | Adjuvant Type | EO No | rate (%) | Control (% kill) 14-day | 28-day |
|---|---|---|---|---|---|
| AE1.3 | SE3 | 16 | 0.0625 | 50 | 50 |
|  |  |  | 0.125 | 56 | 72 |
|  |  |  | 0.25 | 58 | 68 |
| AE1C.3 | Adj2 | 20 | 0.0625 | 39 | 44 |
|  |  |  | 0.125 | 44 | 42 |
|  |  |  | 0.25 | 52 | 51 |

These data indicate a peak or plateau of performance as measured by the % control covering the compounds of the invention.

It is of course to be understood that the invention is not intended to be restricted to the details of the above embodiment which are described by way of example only.

The invention claimed is:

1. An agrochemical formulation, comprising:
   a) a compound or mixture of compounds which is/are ethoxylated fatty acid mono-ester(s) of sorbitan in which the carbon chain length of the fatty acid is from 8 to 14 and the overall degree of ethoxylation is on average from 7 to 16; and
   b) at least two agrochemical actives used in a co-formulation, comprising:
      i) a non-selective herbicide and another type of agrochemical active;
      ii) a selective herbicide and a graminicide;
      iii) a selective broadleaf herbicide and a graminicide; or
      iv) a graminicide and a non-selective herbicide.

2. The agrochemical formulation of claim 1, wherein the formulation is an agrochemical concentrate formulation, or an agrochemical spray formulation formed either by dilution of said concentrate formulation or directly by addition of all the necessary components with water to form the dilute mixture.

3. The agrochemical formulation of claim 1, wherein the ester(s) is/are compound(s) represented by formula (I):

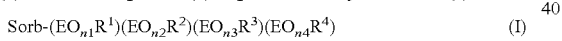

$$\text{Sorb-}(EO_{n1}R^1)(EO_{n2}R^2)(EO_{n3}R^3)(EO_{n4}R^4) \qquad (I)$$

wherein:
   i) Sorb represents a residue obtained by removing four hydroxyl H atoms from sorbitan;
   ii) EO represents an ethyleneoxy residue;
   iii) n1, n2, n3, and n4 each independently represent average values from 0 to 10;
   iv) the total n1+n2+n3+n4 has an average value from 7 to 16; and
   v) $R^1$, $R^2$, $R^3$, and $R^4$ each independently represents H or an acyl group —C(O)—$R^5$, where $R^5$ is a $C_7$ to $C_{13}$ hydrocarbyl.

4. The agrochemical formulation of claim 3, wherein an average of 2.8 to 3.2 of the $R^1$, $R^2$, $R^3$, and $R^4$ groups are H and 0.8 to 1.2 are acyl groups —C(O)—$R^5$.

5. The agrochemical formulation of claim 1, wherein the carbon chain length of the fatty acid is from 10 to 14.

6. The agrochemical formulation of claim 1, wherein:
   i) the non-selective herbicide is one or more of a glyphosate type, a glufosinate type, or a bipyridyl type herbicide;
   ii) the selective broadleaf herbicide is one or more of bentazon, bromoxynil, and 2,4-D amine; or
   iii) the graminicide is one or more acetyl-CoA carboxylase inhibitors.

7. The agrochemical formulation of claim 1, wherein the non-selective herbicide is a glyphosate type herbicide and the selective herbicide is a cyclohexanedione or lipid inhibitor type herbicide.

8. The agrochemical formulation of claim 7, wherein the glyphosate type herbicide is glyphosate in the form of an alkali metal, amine, ammonium or trimesium salt.

9. The agrochemical formulation of claim 7, wherein the cyclohexanedione or lipid inhibitor type herbicide is clethodim.

10. The agrochemical formulation of claim 1, wherein the active is selected from herbicidal active compounds, fungicidal active compounds, insecticidal or acaricidal active compounds, or plant growth controlling compounds.

11. A method of treating crops and/or the soil around a crop, comprising spraying the crop or the soil around the crop with the agrochemical formulation of claim 1.

12. A compound or mixture of compounds which is/are ethoxylated fatty acid mono-ester(s) of sorbitan and are compounds represented by formula (I):

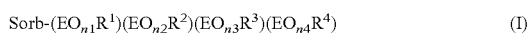

$$\text{Sorb-}(EO_{n1}R^1)(EO_{n2}R^2)(EO_{n3}R^3)(EO_{n4}R^4) \qquad (I)$$

wherein:
   i) Sorb represents a residue obtained by removing four hydroxyl H atoms from sorbitan;
   ii) EO represents an ethyleneoxy residue;
   iii) n1, n2, n3, and n4 each independently represent average values from 0 to 10;
   iv) the total n1+n2+n3+n4 has an average value from 8 to 12; and
   v) $R^1$, $R^2$, $R^3$, and $R^4$ each independently represents H or an acyl group —C(O)—$R^5$, where $R^5$ is a $C_7$ to $C_{13}$ hydrocarbyl.

13. The compound or mixture of compounds of claim 12, wherein an average of 2.8 to 3.2 of the $R^1$, $R^2$, $R^3$, and $R^4$ groups are H and 0.8 to 1.2 are acyl groups —C(O)—$R^5$.

14. The compound or mixture of compounds of claim 12, wherein the sorbitan residue is formed from 1,4-anhydrosorbitol, 1,5-anhydrosorbitol, 3,6-anhydrosorbitol, or any combination thereof.

15. The compound or mixture of compounds of claim 12, wherein the carbon chain length of the fatty acid is from 11 to 13.

* * * * *